US008799202B2

(12) United States Patent
Carroll et al.

(10) Patent No.: US 8,799,202 B2
(45) Date of Patent: *Aug. 5, 2014

(54) PREDICTING STATES OF SUBJECTS

(75) Inventors: Melissa Kristin Carroll, West Windsor, NJ (US); Guillermo Alberto Cecchi, New York, NY (US); Irina Rish, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 110 days.

This patent is subject to a terminal disclaimer.

(21) Appl. No.: 13/523,371

(22) Filed: Jun. 14, 2012

(65) Prior Publication Data

US 2012/0250963 A1 Oct. 4, 2012

Related U.S. Application Data

(63) Continuation of application No. 12/625,707, filed on Nov. 25, 2009, now Pat. No. 8,346,688.

(51) Int. Cl.
  *G06N 5/00* (2006.01)
(52) U.S. Cl.
  CPC ..................................... *G06N 5/003* (2013.01)
  USPC .......................................................... 706/46
(58) Field of Classification Search
  CPC ..................................................... G06N 5/003
  USPC .......................................................... 706/46
  See application file for complete search history.

(56) References Cited

U.S. PATENT DOCUMENTS 7,599,898 B2   10/2009  Tesauro et al.
2009/0210363 A1  8/2009  Grabarnik et al.

OTHER PUBLICATIONS

Rish et al ("Closed-Form Supervised Dimensionality Reduction with Generalized Linear Models" Jul. 2008).*
R. Tibshirani, "Regression Shrinkage and Selection via the Lasso," J.R. Statist. Soc. B, 1996, pp. 267-288, vol. 58, No. 1, Canada.
H. Zou et al., "Regularization and Variable Selection Via the Elastic Net," J.R. Statist. Soc. B, 2005, pp. 301-320, vol. 67, Part 2.
B. Efron et al., "Least Angle Regression," The Annals of Statistics, 2004, pp. 407-499, vol. 32, No. 2.
J. Nelder et al.,"Generalized Linear Models," Journal of the Royal Statistical Society, Series A, 1972, pp. 370-384, vol. 135, Part 3.

(Continued)

*Primary Examiner* — Lut Wong
(74) *Attorney, Agent, or Firm* — Vazken Alexanian; Ryan, Mason & Lewis, LLP

(57) ABSTRACT

Methods for predicting states of a subject are presented. For example, a method for predicting states of a subject includes obtaining training data comprising a plurality of variables, obtaining training states associated with the training data, and forming a predictive model according to the training data and the training states, the predictive model predictive of the training states. The forming of the predictive model includes extracting one or more hidden components from the training data. The extracting of the one or more hidden components includes regression analysis including determining one or more relationships between the one or more hidden components and the plurality of variables, and determining one or more relationships between the one or more hidden components and the training states. A number of the one or more hidden components is less than a number of the plurality of variables and greater than a number of the training states.

9 Claims, 6 Drawing Sheets

(56) References Cited

OTHER PUBLICATIONS

A. Orlitsky et al., "Supervised Dimensionality Reduction Using Mixture Models," Proceedings of the 22nd International Conference on Machine Learning (ICML), 2005, 8 pages, Germany.

F. Pereira et al., "The Support Vector Decomposition Machine," Proceedings of the 22nd International Conference on Machine Learning (ICML), 2006, 8 pages, Pennsylvania.

K.Q. Weinberger et al., "Metric Learning for Kernel Regression," AISTATS, 2007, 8 pages.

M. Yuan et al., "Model Selection and Estimation in Regression with Grouped Variables," Journal of the Royal Statistical Society, Series B, 2006, pp. 49-67, vol. 68, Part 1.

H. Binder et al., "Allowing for Mandatory Covariates in Boosting Estimation of Sparse High-Dimensional Survival Models," BMC Bioinformatics, Jan. 2008, pp. 1-10.

A. Tenenhaus et al., "Kernel Logistic PLS: A Tool for Supervised Nonlinear Dimensionality Reduction and Binary Classification," Computational Statistics and Data Analysis, May 2007, pp. 4083-4100.

M. Slawski et al., "CMA—A Comprehensive Bioconductor Package for Supervised Classification with High Dimensional Data," BMS Bioinformatics, Oct. 2008, pp. 1-17.

M. Pechenizkiy et al., "Local Dimensionality Reduction and Supervised Learning within Natural Clusters for Biomedical Data Analysis," IEEE Transactions on Information Technology in Biomedicine, 2006, pp. 1-7.

C. Carvalho et al., "High-Dimensional Sparse Factor Modelling: Applications in Gene Expression Genomics," Journal of the American Statistical Association, Dec. 2008, 51 pages.

S. Balakrishnan et al., "Algorithms for Sparse Linear Classifiers in the Massive Data Setting," Journal of Machine Learning Research, Jun. 2008, pp. 313-337, vol. 9.

M.K. Carroll et al., "Prediction and Interpretation of Distributed Neural Activity with Sparse Models," NeuroImage, 2008, pp. 112-122, vol. 44.

I. Rish et al., "Closed-Form Supervised Dimensionality Reduction with Generalized Linear Models," Proceedings of the 25th International Conference on Machine Learning, 2008, pp. 832-839, Helsinki, Finland.

\* cited by examiner

200

300

600

GENERALIZED LINEAR MODELS (GLMs)

$$E(X_d) = f_d^{-1}(UV_d)$$
$$E(Y_k) = f_k^{-1}(UW_k)$$

f = LINK FUNCTION DEFINED BY THE CORRESPONDING EXPONENTIAL-FAMILY:
 IDENTITY FUNCTION $f(\mu) = \mu$ — GAUSSIAN (LINEAR REGRESSION)
 LOGIT FUNCTION $f(\mu) = \text{LOG} \frac{\mu}{1-\mu}$ — BERNOULLI (LOGISTIC REGRESSION)

PREDICTING STATES OF SUBJECTS

CROSS-REFERENCE TO RELATED APPLICATION(S)

This application is a continuation of pending U.S. application Ser. No. 12/652,707, filed on Nov. 25, 2009, the disclosure of which is incorporated herein by reference.

FIELD OF THE INVENTION

The present invention relates generally to predictive modeling and, more particularly, to predictive modeling comprising sparse regression and supervised component analysis with dimensionality reduction.

BACKGROUND OF THE INVENTION

Recent advances in medical imaging technology have introduced functional magnetic resonance imaging (fMRI) capable of acquiring sequences of images of brain activity (data) by measuring changes in blood oxygenation levels. The acquired data may comprise a very large number of voxels or variables taken at many points in time.

Predicting mental states, including mental disease states, is a goal of brain studies. Indicating current mental states or predicting future mental states, including response to therapy, is useful in the treatment of mental diseases.

Key challenges in the analysis of biological data, including brain related data, are the very high dimensionality of the data, the temporal nature of underlying processes and the complicated, and not necessarily well understood, relationship between the environment or other stimuli and the state of the biological system, for example, the brain.

Because of the typically large amounts of data generated by medical imaging, statistical methods are often used for analyzing medical imaging data. Such statistical methods may include regression analysis, least absolute shrinkage and selection operator methods, elastic net methods, and least angle regression selection methods.

SUMMARY OF THE INVENTION

Principles of the invention provide, for example, methods and apparatus for predicting one or more states of a subject.

In accordance with one aspect of the invention, a method for predicting one or more states of a subject comprises obtaining training data comprising a plurality of variables, obtaining one or more training states associated with the training data, and forming a predictive model according to the training data and the one or more training states, the predictive model predictive of the one or more training states. The forming of the predictive model comprises extracting one or more hidden components from the training data. The extracting of the one or more hidden components comprises regression analysis comprising determining one or more relationships between the one or more hidden components and the plurality of variables, and determining one or more relationships between the one or more hidden components and the one or more training states. A number of the one or more hidden components is less than a number of the plurality of variables and greater than a number of the one or more training states. One or more of the obtaining of the training data, the obtaining of the one or more training states, and the forming of the predictive model are implemented as instruction code executed on a processor device.

In accordance with another aspect of the invention, a system for predicting one or more states of a subject is provided. The system comprises modules for implementing the above method.

In accordance with an additional aspect of the invention, apparatus for predicting one or more states of a subject is provided. The apparatus includes a memory and a processor coupled to the memory. The apparatus is operative or configured to perform the above method.

In accordance with another additional aspect of the invention, an article of manufacture for predicting one or more states of a subject is provided. The article of manufacture tangibly embodies a computer readable program code which, when executed, causes the computer to implement the above method.

Exemplary aspects of the invention include general purpose methods for discovering sparse patterns in high-dimensional data. Exemplary applications include medical imaging, including functional magnetic resonance imaging data analysis. Embodiments of the invention are useful, for example, in processing large amounts of data, such as data produced in conjunction with, or during analysis of, functional magnetic resonance imaging.

These and other features, objects and advantages of the present invention will become apparent from the following detailed description of illustrative embodiments thereof, which is to be read in connection with the accompanying drawings.

DETAILED DESCRIPTION OF THE INVENTION

Figure 1:
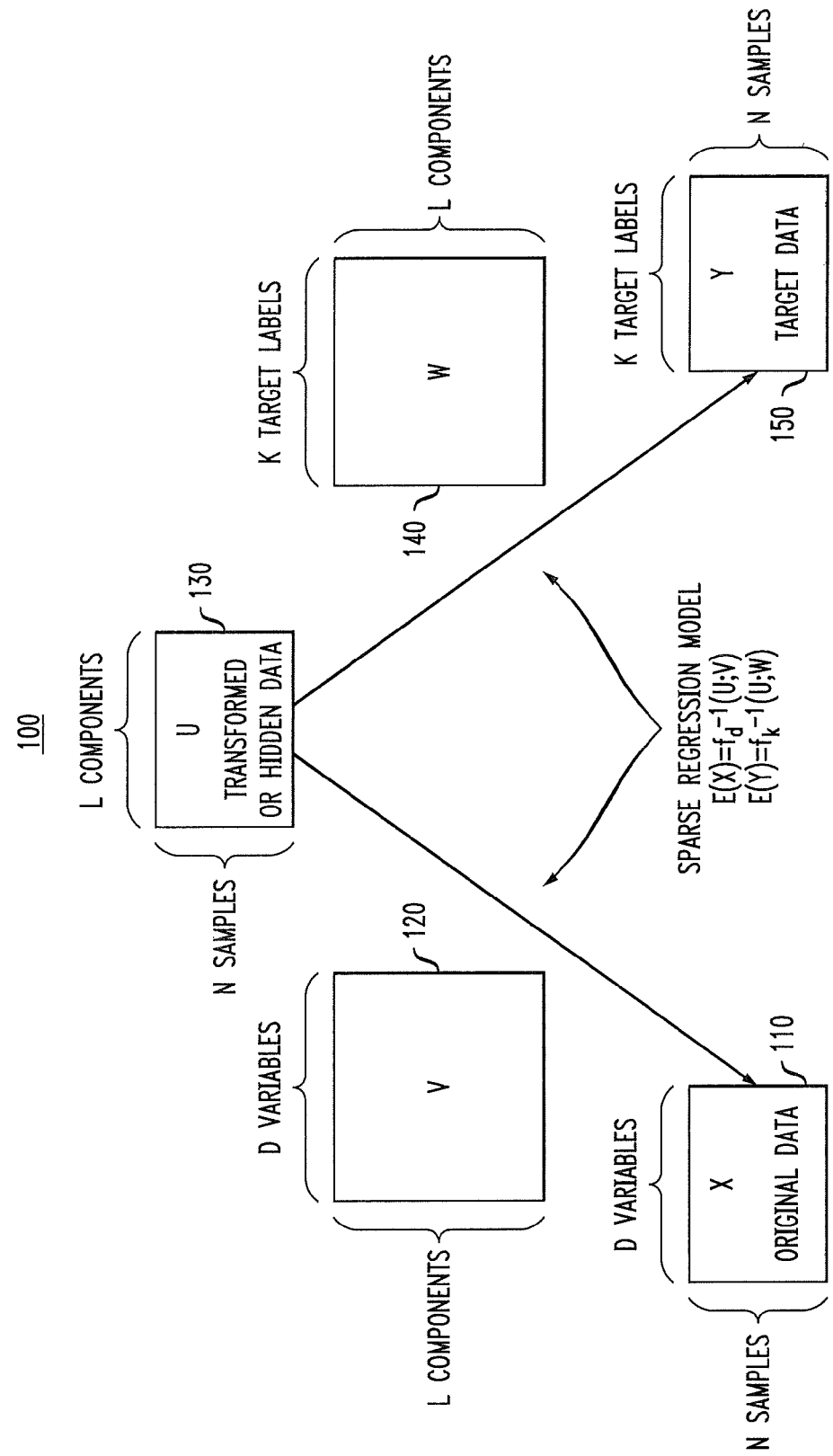
FIG. 1 is a mapping diagram illustrating matrices, data, variables and mapping of variables of a predictive model according to an exemplary embodiment of the invention.

It is to be appreciated that the techniques of the present invention are not limited to the specific method, systems and techniques shown and described herein. Rather, principles of the invention are directed broadly to predictive modeling and techniques for discovering predictive patterns in high dimensional data. For this reason, numerous modifications can be made to the embodiments shown that are within the scope of the present invention. No limitations with respect to the specific embodiments described herein are intended or should be inferred.

Exemplary embodiments of the present invention are described herein with reference to the field of fMRI to illustrate and provide a specific domain for application of the disclosed techniques. However, embodiments of the invention are applicable to other fields where predictive modeling or pattern extraction is desired. Some exemplary embodiments of the present invention relate to brain, brain states, brain activity and diseases of the brain. The invention is not so limited, other organs of a body, and states, activities and diseases associated with other organs of the body are contemplated. Where embodiments, methods and techniques of the invention are applied to brain or brain states, activities or diseases, similar embodiments, methods and techniques of the invention may be applied to other organs or systems of the body or associated states, activities or diseases. Furthermore, embodiments of the invention are not limited to brain, bodies, organs and human or animal systems. Application of embodiments of the invention to non-living entities and systems is also contemplated.

Aspects of the invention include, for example, general purpose methods for discovering sparse patterns (e.g., features or components) in high-dimensional data. Exemplary applications include medical imaging, including fMRI data analysis. Other applications are contemplated, including, but not limited to, application to other life sciences areas including microarray data analysis, and application to system performance management and prediction based on high dimensional measurements of characteristics of a system.

Magnetic Resonance Imaging (MRI) is an imaging technique to visualize the internal structure and/or function of a body. MRI provides higher contrast between the different soft tissues of the body than provided by many other imaging techniques. Consequently, MRI is useful in neurology and brain imaging. MRI is also useful for imaging other portions of the body, for example, musculoskeletal, cardiovascular, and for oncological (cancer) imaging. MRI does not use ionizing radiation, but uses a powerful magnetic field to align the nuclear magnetization of, for example, hydrogen atoms in water in the body. Radio frequency (RF) fields are used to systematically alter the alignment of this magnetization, causing the hydrogen nuclei to produce a rotating magnetic field detectable by the scanner. This signal can be manipulated by additional magnetic fields to build up enough information to construct an image of the body or portions thereof.

Functional magnetic resonance imaging (fMRI) is a type of specialized MRI. fMRI, for example, measures the hemodynamic response (i.e., response to the dynamic regulation of the blood flow in the brain) related to neural activity in the brain or spinal cord of humans or other animals. Neurons require energy to function. This energy is supplied in the form of glucose and oxygen carried in hemoglobin. The blood supply of the brain is dynamically regulated to give active neural assemblies more energy while inactive neural assemblies receive less energy. Therefore, changes in blood flow and blood oxygenation in the brain (collectively known as hemodynamic) are closely linked to neural activity. When nerve cells are more active they consume more oxygen carried by hemoglobin in red blood cells from local capillaries. The local hemodynamic response to this oxygen utilization is an increase in blood flow to regions of increased neural activity, occurring after a delay of, for example, 1-5 seconds. This local hemodynamic response may rises to a peak over, for example, 4-5 seconds before falling back to near baseline levels, leading to local changes in the relative concentration of oxyhemoglobin and deoxyhemoglobin and changes in local cerebral blood volume in addition to this change in local cerebral blood flow. Therefore, fMRT may, for example, produce images of brain activity by measuring changes in blood oxygenation levels and/or other hemodynamic responses.

A voxel is a volume element, representing a value, a structure or a three-dimensional image on a three-dimensional grid. A voxel is analogous to a pixel, which represents two-dimensional image data. Voxels are frequently used in the visualization and analysis of medical and scientific data. As with a pixel, a voxel itself typically does not comprise spacial position or coordinates of the voxel. Rather, spacial position of a voxel is inferred based on the position of the voxel relative to other voxels (e.g., the position in the data structure that makes up a single volume image). The word voxel is a linguistic blend of the words volumetric and pixel.

The Least Absolute Shrinkage and Selection Operator (Lasso) method is a shrinkage and/or selection method for linear regression. The Lasso method may minimize the usual sum of squared errors, with a bound on the sum of the absolute values of the coefficients. The Lasso may be associated with soft-thresholding of wavelet coefficients, forward stagewise regression, and boosting methods. The Lasso method is described in the paper: Tibshirani, R, *Regression Shrinkage and Selection via the Lasso*, J. Royal. Statist. Soc B., Vol. 58, No. 1, 1996, pages 267-288, the disclosure of which is incorporated herein by reference.

The Elastic Net method is described in the paper: Zou, H. and Hastie, T.; *Regularization and Variable Selection via the Elastic-net*; J. R. Statist. Soc. B 2005; vol. 67, pages 301-320, the disclosure of which is incorporated herein by reference. The Elastic Net is a regularization and variable selection method. The elastic net encourages a grouping effect, where strongly correlated predictors tend to be in or out of an associated model together. The elastic net is particularly useful when the number of predictors is much bigger than the number of observations. A least angle regression selection-elastic net (LARS-EN) algorithm can compute elastic net regularization paths efficiently, much like a least angle regression selection (LARS) method or algorithm does for the LARS-EN regression. The LARS method is described in the paper: Efron, B., et al.; *Least Angular Regression*; the Annals of Statistics 2004; vol. 32, No. 2, pages 407-499, the disclosure of which is incorporated herein by reference. LARS is a linear model selection algorithm. A LARS algorithm may implement the Lasso method. A LARS algorithm may implement forward stagewise linear regression and use a piecewise linear solution path using a modification of forward stagewise and least angle regression paths. An exemplary advantage of LARS is short computation.

Supervised learning is a machine learning technique for deducing a function from training data. The training data consist of pairs of input objects and target outputs. The input objects are typically vectors or voxels, for example, fMRI data. The deduced function may comprise a regression or a prediction of a class label (e.g., target label) of the input object. An exemplary task of the supervised learner is to predict the value of the function for any valid input object after having seen a number of training examples (i.e. pairs of input objects and target output). The learner, for example, may have to generalize from the presented data to unseen situations in a reasonable way (e.g., using inductive bias).

Component analysis is a statistical method of identifying hidden structure or components in data. One exemplary goal of component analysis is identifying a more meaningful basis (e.g., the most meaningful basis) to re-express observed data. In so doing, an objective is that this new basis will filter out noise and reveal hidden structure. Component analysis may reduce the number of variables (i.e., the number of identified hidden components is less than the number of observed variables) and detect structure in relationships among variables (e.g., to classify variables). Principle component analysis and independent component analysis are exemplary types of component analysis that are well known in the art. Principle component analysis comprises a mathematical procedure that transforms a number of possibly correlated variables (e.g., observed variables) into a smaller number of uncorrelated variables called components or principle components. For example, the first principal component may account for as much of the variability in the data as possible, and each succeeding component may account for as much of the remaining variability as possible. A principal component may, for example, be defined as a linear combination of optimally-weighted observed variables. Independent component analysis is a statistical technique for decomposing a complex dataset into independent sub-parts.

In statistics, regression analysis includes techniques for modeling and analyzing several variables to determine relationships among a dependent variable and one or more independent variables. Regression analysis may indicate how a value of the dependent variable changes when any one of the independent variables is varied, while the other independent variables are held fixed. Regression analysis may estimate the conditional expectation of the dependent variable given the independent variables, that is, the average value of the dependent variable when the independent variables are held fixed. Regression analysis may indicate which among the independent variables are related to the dependent variable, and to explore the forms of these relationships. Linear regression, least squares methods and Bayesian methods are exemplary methods of regression analysis.

Sparse regression is a method of regression analysis that transforms a total number of variables, which may potentially be related to a dependent variable, into a smaller number of variables (e.g., a much smaller number of variables or less than about 10% of the number of variables) related to the dependent variable. A sparse regression may be considered as a regression using a parsimonious subset of all available input data variables for an efficient prediction of a target variable. For example, the total number of variables may be variables associated with high-dimensional measured or original data (e.g., fMRI data). High-dimensional data, for example, may comprise relatively many variables (e.g., 10,000 or more) but, sometimes, relatively few samples (e.g., 700 or less). Sparse regression may be applied such that the smaller number of variables related to a plurality of dependent variables are formed or selected from the total number of variables. Methods of sparse regression include, for example, L1-regularization, Lasso, Elastic Net and group Lasso. Sparse regression may comprise selection of the smaller number of variables related to the plurality of dependent variables from the existing variables by assigning non-zero weights to important or significant variables only (e.g., to those variable of observed data that are predictive of the target variable).

A sparse matrix is a matrix populated primarily with zeros (i.e., more than one-half of the data within the matrix equals zero). Conceptually, sparsity may correspond to systems which are loosely coupled. Consider a line of balls connected by springs from one to the next. This is a sparse system and may be represented by a sparse matrix having non-zero elements only in X-Y positions corresponding to the coupling between adjacent balls, and having zero elements in X-Y positions corresponding to couplings between non-adjacent balls. By contrast, if the same line of balls had springs connecting every ball to every other ball, the system would be represented by a non-sparse or dense matrix.

The generalized linear model (GLM) is a flexible generalization of ordinary least squares regression. The GLM generalizes linear regression by allowing the linear model to be related to the response variable via a link function and by allowing the magnitude of the variance of each measurement to be a function of its predicted value. Generalized linear models were formulated as a way of unifying various other statistical models, including linear regression, logistic regression, Poisson regression and others, under one framework. This allows for a general algorithm for maximum likelihood, or minimized regularized loss, estimation in all of these models. It may be extended to encompass other statistical models as well. Generalized linear models are described by John Nelder and Robert Wedderburn in *Generalized Linear Models*, Journal of the Royal Statistical Society, Series A (General) vol. 135 (3), pages 370-384, 1972; the disclosure of which is incorporated herein by reference.

Given data, model parameters of a GLM regression are found by maximizing log-likelihood (or, equivalently, minimizing negative log-likelihood) of the data under a particular assumption about noise. The type of noise uniquely defines the member of the GLM regression family (e.g., Gaussian noise corresponds to ordinary linear regression, Bernoulli noise gives rise to logistic regression, etc.). The negative log-likelihood, i.e., the objective function in the above minimization problem, is also called the loss function. Sparse GLM regression incorporates a weighted penalty to this loss function, the so-called L1-regularization that is defined as a sum of absolute values of the unknown regression parameters (i.e., the variables we are optimizing over), multiplied by a weight called the regularization constant or parameter, or sparsity constant or parameter. This parameter controls the level of sparsity, i.e. the number of nonzero elements in the solution to the above optimization problem, i.e., in the resulting vector of model parameters. Regularized loss is expressed as a loss function (e.g., a regularized loss function) comprising the weighted penalty, the so-called L1-regularization.

Logistic regression (also referred to as a logistic model or logit model) is used to predict the probability of occurrence of an event by fitting data to a logistic curve. Logistic regression may be, for example, a GLM used for binomial regression. Like many forms of regression analysis, logistic regression makes use of several predictor variables that may be either numerical or categorical. For example, the probability that a person has a heart attack within a specified time period might be predicted from knowledge of the age, gender and body mass index of the person.

As used herein in the broad sense, term states or states of a subject means the one or more properties, attributes or characteristics of a subject that may be predicted by data obtained from the subject. By way of example only, states of a subject may comprise brain states and may be predicted based upon fMRI data obtained from the brain of a subject. Other non-limiting examples of states include: illnesses, properties, attributes or characteristics of a human or other organism, and properties, attributes or characteristics of non-living entities.

The term brain state, as used herein, may comprise, but is not limited to, one or more of the following: the mental or cognitive state of a subject, a mental or brain disease state, a brain response to a stimulus, a brain response to a physical or mental task, a response to an emotion, a response to sensatory input, and any other state related to the brain that is discernable using measurement techniques (e.g. fMRI) associated with embodiments of the invention. By way of non-limiting examples only, a brain state may include one or more of: a brain state associated with an emotion (e.g., anger, excitement, happiness, sadness, anxiousness, or annoyance), a brain state associated with a sensation (e.g., a sight, hearing, smell, touch or taste), a brain state associated with a disease, (e.g., schizophrenia, depression, Alzheimer's, dementia or other mental or brain disease), and a brain state associated with a target label of fMRI data or associated with a specific stimulus intended to evoke a brain response, such as a brain response determined by fMRI (e.g., auditory stimulus such as words or sounds, visual stimulus such as pictures, or activity of a person such as playing a video-game).

Key challenges in analysis of biological data, such as medical imaging (e.g., fMRI) include high dimensionality of data, and complicated relationships between different stimuli and a "state of the biological system" that need to be modeled.

Embodiments of the invention are useful, for example, in processing large amounts of data, such as data produced in conjunction with, or during analysis of, functional magnetic resonance imaging (fMRI). fMRI measurements can give rise to very large amounts of data, for example, consisting of tens of thousands or hundreds of thousands of voxels included in hundreds or thousands of samples, for example, samples taken at different time points.

According to aspects of the invention, fMRI may be used to scan the brains of subjects, for example, while the brains are receiving stimuli or when brains are diseased or have other states. Embodiments of the invention provide for learning tasks. For example, a model including or representing fMRI data of brain scans learns (forms) parameters such that the model is useful in predicting mental or brain states. The model may, for example, extract or form parameters representative of mental or brain states from measured data (e.g., fMRI data).

According to aspects of the invention, fMRI data may be used to predict brain states; to discriminate between brain states of a person, for example brain or mental states associated with a person looking at a face or at a building, a person listening to a phrase in a first language or a phrase in a second language, a person performing a mental or physical task or different mental or physical tasks, or a person having one or other emotion; or to predict brain activity given a specific stimulus.

As an example of an embodiment of the invention, consider training a model and subsequent prediction by the model. The training may, for example, comprises two, three or more runs through a virtual reality sequence or video game. fMRI data is obtained from each run, for example, continuous or periodic snapshot fMRI data. Each run is rated on a number of target features, for examples, subjective target features (annoyance, sadness and anxiety) and objective target features (presentation of objects or representation of objects such as a dog, presentation of visual stimuli such as faces, presentation and/or fulfillment of instructions, and successful completion of tasks or successful responses). After the training, the model is useful in predicting brain states, for example, brain states associated with the target features mentioned above. The training may be performed using data obtained from the same or different subject as the subject undergoing the prediction process (i.e., test subjects). The trained model models brain or mental states of the training subjects or other test subjects.

An exemplary advantage of the invention is interpretability of, and predictions by, a model that results from application of sparse regression. The model may indicate which subsets of voxels or brain areas are most relevant to prediction of future brain states.

In many practical applications (e.g. in computational biology and medical imaging) modern measurement techniques, (e.g., fMRI for brain imaging) provide very high-dimensional measurements (e.g., voxels, such as voxels representing a 3D brain image). However, such measurements may not be necessarily at an optimum or desired level of abstraction to model or predict a phenomenon of interest (e.g., absence or presence of a disease in a patient or a brain state).

A challenge is to form an appropriate representation of the data (i.e., extract predictive features or patterns) that captures the essence of the phenomenon that is being modeled or predicted. This challenge may arise in many areas of application of machine learning and, for example, may be conventionally approached in an ad-hoc manner by designing domain-specific features based on expert knowledge.

Consider, for example, predicting brain states. For a first example, consider a brain state associated with a target label or target variable of fMRI data. The target label may comprise aspects that are, for example, mental or environmental (e.g., the presence of a danger in a videogame that a subject is currently playing). fMRI data may consist of, for example, a sequence of three-dimensional (3D) brain images taken within some time interval. The brain images are typically very highly dimensional. An exemplary objective of the present invention is to discover brain activation patterns that are most relevant to predicting the mental states. For a second example, consider analysis of fMRI data in order to discriminate between healthy subjects and subjects having certain mental illness, for example schizophrenia. In these exemplary examples of application of methods of the invention, an objective of data analysis is to design, form or discover biomarkers. In this sense, biomarkers are, for example, patterns or features that are predictive regarding the concept or brain states of interest.

Brain data (e.g., fMRI data) may be analyzed by independently estimating correlations between a target variable that is to be predicted and each voxel, and forming and analyzing an activation map from the correlations. However, such analysis may fail to discover certain predictive patterns. Moreover, voxels may correspond to somewhat arbitrary partitioning of a brain and may not provide the optimum or desired level of representation of the brain. An alternate approach to brain modeling is based on prior-knowledge about functionality of different brain areas. Such prior knowledge may be incomplete or only partially correct. Approaches based solely or mostly on prior knowledge may not be flexible enough to incorporate information from obtained data and may not allow discovery of new biomarkers.

Sparse optimization techniques, such as Lasso, have become popular due to incorporated variable-selection properties. However, such sparse optimization techniques only select variables from the set of given raw measurements, and are unable to construct new features (e.g., new features comprising or derived from variables of the raw measurements), often leading to somewhat arbitrary selection of variables from a group of related variables that should have been included together to yield a meaningful model. This is a know limitation of Lasso-like approaches. Enhancements to Lasso approaches attempt to resolve the above deficiency by including groups of related variables in the model (e.g., a group Lasso model). However, a significant drawback remains; the enhanced Lasso approaches require that groups of related variables are specified in advance, contrary to the desire to discover or form such groups of related variables as a consequence of analysis. Aspects of the invention address the above limitations and provide a way to learn predictive patterns, such as groups of related variables or new features or components, thus avoiding limitations of Lasso and group Lasso approaches. Also avoided are limitations of manual (expert-knowledge-based) feature selection, and potential drawbacks of using original, raw measurements that may not provide an interpretable model of underlying phenomena.

Other exemplary aspects of the invention include extracting sparse patterns as subsets of original variables. The sparse patterns may, for example, allow for meaningful interpretation of a resulting model. Non-sparse supervised dimensionality reduction methods involve all variables with non-zero weights and thus are much less interpretable.

Methods of the invention, for example, may combine prior knowledge with learning from data. For example, a model may be initialized using neuro-scientific knowledge about brain activation patterns, and then refined or modified using or learning from the data (i.e., original data).

Exemplary aspects of the invention include an automated extraction of predictive features or patterns while learning a predictor. Methods of the invention may comprise, for example, sparse regression, and supervised dimensionality reduction and component analysis, (i.e., dimensionality reduction/component analysis by supervised learning), for feature or component extraction. Methods of the invention comprising sparse regression and supervised dimensionality reduction and component analysis are herein called Sparse Supervised Component Analysis (SSCA). SSCA is superior to techniques that only filter out variables of voxels that have low correlation with the target variable, because such filtering techniques may fail to discover certain predictive patterns or components. SSCA is superior to Lasso because, for example, SSCA can select features over groups of variables that are new features or new patterns. Lasso may only select from the original or raw data and is unable to construct new features. Group Lasso requires that groups of related variables are specified in advance. The groups of related variables need to be discovered and therefore cannot be specified in advance. SSCA may use new features (e.g., new features comprising, extracted or derived from original variables) that are constructed automatically. Sparse regression aspects of SSCA enhance interpretability of extracted features. SSCA provides analysis of analog (e.g., real-valued or continuous) and binary (e.g., discrete) data and labels.

FIG. 1 is a mapping diagram illustrating matrices, data, variables and mapping of variables of a predictive model 100 according to an embodiment of the invention. Matrix X 110 is an N×D matrix of original data, for example fMRI brain data. Other types of original data are contemplated, for example, data about genes, data from organs other than brain, data from human, animal and plant organisms, environmental data and data from non-living entities. Matrix X 110 comprises N rows and D columns Each row corresponds to or comprises a sample of data, for example, a sample comprising a 3D image (e.g., fMRI image) of a brain. Typically, but not necessarily, a sample corresponds to data obtained at a particular time. Each column corresponds to a variable that the sample of data comprises (i.e., comprises in each row). For example, a datapoints in a particular column may comprise the intensity of a voxel of fMRI data representing a particular spatial coordinates within the brain, and a datapoints in a particular column and a particular row may comprise the intensity of a voxel of fMRI data representing a particular spatial coordinates within the brain at a particular time. Other datapoints in the same column may represent the intensity of the voxel at different points in time. Other data points along a row may represent the intensity of other voxels representing other spatial coordinates within the brain. Characteristics of voxels, other than intensity, are also contemplated, for example, color. Matrix Y 150 comprises an N×K matrix of target data. Matrix Y 150 comprises N rows and K columns Each row of matrix Y 150 corresponds to a row of matrix X 110 (e.g., a row of matrix Y 150 corresponds to a row of matrix X 110 having the same row position within the matrices). For example, if the rows of matrix X 110 represent points in time, corresponding rows of matrix Y 150 represent the same points in time. Each column of matrix Y 150 corresponds to a target label (also called a target variable or classification) of interest, that is, a target label that is to be predicted from test data in matrix X 110 during the predicting mode. Target labels are classifications characterizing the subject represented by the original data, such as original learning data and original predictive data for a subject under study. During learning or training, the target labels comprise know characteristics corresponding to the subject of training data in matrix X 110. For training, target labels are provided along with training data (training data in matrix X 110), and the correspondence of the target labels to the subject of the training data is known and provided. In the prediction mode, the target labels comprise potential characteristics that may or may not correspond to a subject under study or test (i.e., the subject of the prediction) represented by matrix X 110 or by a vector of test data. Note that, in most cases, not all of the target labels will correspond to a test subject. By way of example only, target labels may correspond to classifications into one or more brain states, such as schizophrenia, depression, happiness sadness, etc. (see exemplary list of brain states previously stated).

The original D-dimensional data representation (i.e., matrix X 110) is mapped into a new L-dimensional representation of transformed data described by a matrix U 130. The transformed data can be considered or termed hidden or unobserved data in that it is not directly observed in matrices X 110 or Y 150. Hidden data may comprise hidden or unobserved components, patterns, variables or dimensions, within the original data, that are not readily observable without analysis of the original data to extract the hidden components patterns, variables or dimensions. The terms components and hidden components will be used synonymously herein as a collective term having meaning inclusive of hidden or unobserved components, patterns, variables and dimensions.

To visualize a transformation of the original data, consider the rather trivial, non-limiting example of a mapping or transformation of 3-dimensional original observed (e.g., measured) data into a new 2-dimensional representation. The three axes of the original three dimensions may be non-perpendicular. The original data may be 100 data points that, when viewed along any of the three axes, present no particular pattern; thus, the original data may not readily provide desired information. The original 3-dimensional data is transformed into a 2-dimensional representation in X and Y dimensions having X and Y axes. When viewed along the X axis, the transformed data points are observed to have a particular pattern, for example to substantially fall on a broad straight line having a particular direction in X-Y space. Thus the transformed data more readily provides the desired information (e.g., the linear pattern). The X and Y dimensions may be considered, for example, to be components. Such components are hidden or unobserved (i.e., unobserved in the original data), in contrast to the original data and the dimensions of the original data which are observed in some way, for example, measured). The original data is, therefore, considered observed data with observed dimensions.

Methods of the invention comprise constructing a mapping from the original D-dimensional data (i.e., matrix X 110) into a new L-dimensional representation described by matrix U 130 comprising extracted components. Matrix U 130 comprises N rows and L columns. Each row of matrix U 130 corresponds to a row of matrix X 110 (e.g., a row of matrix U 130 corresponds to a row of matrix X 110 having the same row position within the matrices). Each column of matrix U 130 corresponds to a component (e.g., a dimension) within each row of matrix U 130. Each component is derived or transformed from variables of the original data (i.e., matrix X 110). For example, each component of matrix U 130 may be selected from the D variables of matrix X 110 using sparse regression, or using sparse regression during supervised learning. The mapping between matrix X 110 and matrix U 130 is according to, or described by, matrix V 120 having L rows and D columns Each column of matrix V 120 corresponds to a column of matrix X 110, and each row of matrix V 120 corresponds to a column of matrix U 130.

Matrix U 130 is mapped into matrix Y 150 according to or described by matrix W 140 having L rows and K columns. Each column of matrix W 140 corresponds to a column of matrix Y 150, and each row of matrix W 140 corresponds to a column of matrix U 130. The mappings from matrix X 110 to matrix U 130 and from matrix U 130 to matrix Y 150 may occur substantially simultaneously.

Matrices U 130, V 120 and W 140 are sparse matrices. The sparsity is enforced on matrices U 130, V 120 and W 140 by sparse regression and supervised component analysis according to methods of the invention.

Matrix U 130 may be called a mixing matrix because matrix U 130 may contain weights (e.g., regularization or sparsity constants or parameters) of each component for one or more samples.

Exemplary sparse regression models are represented by $E(X)=f_d^{-1}(U;V)$ and $E(Y)=f_k^{-1}(U;W)$, where function $f_d^{-1}$ is the inverse of function $f_d$, and function $f_k^{-1}$ is the inverse of function $f_k$. Functions $f_d$ and $f_k$ are link functions of GLMs. E(X) and E(Y) are the expectations of matrix X 110 and matrix Y 150, respectively. By way of example only, link functions $f_d$ may be a link function associated with a linear regression and $f_k$ may be a link function associated with a logistic regression.

Matrix X 110 may be generated as a function of matrices U 130 and V 120 (e.g., from matrix U 130 according to matrix V 120). Matrix Y 150 may be generated as a function of matrices U 130 and W 140 (e.g., from matrix U 130 according to matrix W 140).

Sparsity is enforced on matrices U 130, V 120 and W 140 by combining sparse regression with supervised component analysis. The sparse regression approaches include, for example, L1-regularized linear regression, and a generalized linear model with L1-regularization. The sparsity of matrices U 130, V 120 and W 140 provides interpretability of extracted features or of a model. For example, a sparse row of matrix V 120 represents a subset of variables of the original data (i.e., matrix X 110) that corresponds to a particular component (e.g., a pattern, or an extracted feature). For another example, sparse rows of matrix V 120 can be interpreted in the context of fMRI analysis as subsets of voxels that yield patterns of brain activation relevant to or predictive of the phenomenon that is to be predicted (e.g., phenomenon related to one or more target labels). Consequently, the extracted patterns of brain activation (components) i.e., the sparse rows of matrix V 120, may be used as biomarkers for such phenomenon. For an additional example, sparsity of matrix W 140 corresponds to selection of subset of patterns or components (i.e., components from matrix U 130) necessary to predict one or more target variables of matrix Y 150 (e.g., target variables associated with brain states).

Because methods of the invention may comprise sparse optimization for enforcing selection of small subsets of variables, and supervised component analysis for constructing new components from data, a collection of components may be provided, each corresponding to sparse subsets of original variables (e.g., potentially overlapping sparse subsets). The collection of components may predict one or more target variables.

Matrix U 130 can be viewed as a new representation of N data samples via new L components (e.g., new extracted features or patterns). A sparse row of matrix U 130 corresponds to selecting a subset of components in matrix V 120 whose weighted combination corresponds to sample (i.e., a row) in matrix X 110. Similarly, a sparse row of matrix W 140 corresponds to selecting a subset of components in matrix U 130 necessary to predict matrix Y 150. Sparsity of matrix W 140 corresponds to selection of subset of components necessary to predict Y 150 (e.g., target labels in matrix Y 150).

Exemplary methods of the invention (e.g., methods according to the mapping diagram 100) may predict, after training, one or more target variables (e.g., target variables associated with brain states) from original data (i.e., matrix X 110).

Figure 2:
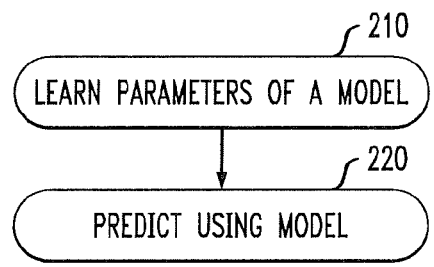
FIG. 2 illustrates a method for predicting one or more states of a subject according to an exemplary embodiment of the invention.

FIG. 2 illustrates a method 200 for predicting one or more states of a subject according to an embodiment of the invention. Predicting comprises modeling states of the subject (e.g., brain states); therefore, method 200 may also be considered as a method of modeling states of a subject according to embodiments of the invention. Step 210 comprises learning parameters of a predictive model and is described in detail below with reference to FIGS. 3 and 4. Step 220 comprises predicting states of a subject using the model and is described in detail below with reference to FIG. 5. Step 210 may be referred to as the learning or training mode and step 210 may be referred to as a predicting or test mode.

Figure 3:
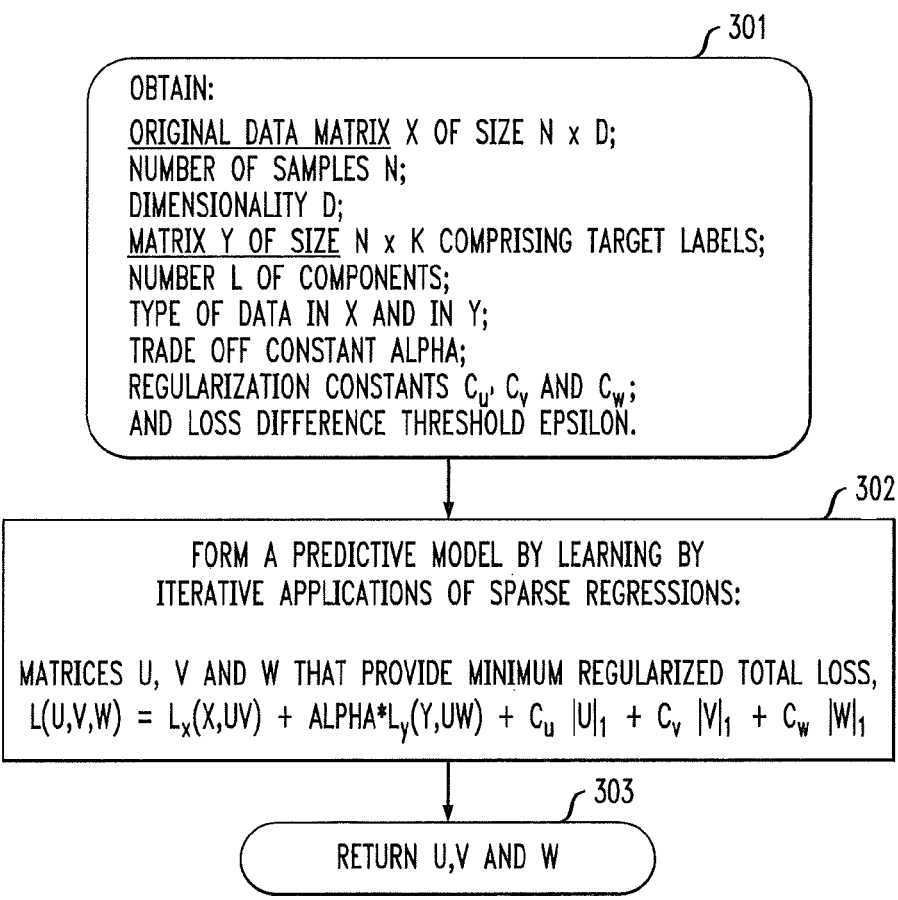
FIG. 3 illustrates a method for learning a sparse supervised component model according to an exemplary embodiment of the invention.

FIG. 3 illustrates a method 300 for learning a sparse supervised component model (SSC model) according to methods of the invention. Method 300 may be considered as a method forming a predictive model according to training data and training states. The predictive model being predictive of the training states Method 300 may be considered an implementation of step 210 of method 200.

Step 301 comprises inputting or providing data for the model. The data provided comprises: original data matrix X 110 of size N×D; the number of samples N in the data matrix X 110; the dimensionality D of the data matrix X 110 (e.g., the dimensionality of the samples in data matrix X 110); a matrix Y 150 of size N×K representing the target labels; a number L of components (e.g., the number of L components of matrix U 130); a type of data in matrix X 110 and a type of data in matrix Y 150 (e.g., binary or analog); a tradeoff constant, alpha; regularization constants Cu, Cv and Cw; and a loss difference threshold epsilon. The original data is data to be used for training the model, for example, for the model to learn matrices U 130, V 120 and W, 140. Matrix Y comprises target labels that have a known correspondence to the original data. During training, at least one of the target labels is a training state (i.e., a known and provided state, such as a known brain state of a subject from which the training data came). For example, if the original data is fMRI data from a subject known to have a specific brain state (i.e., the training state) when at least a specific portion of the original data was obtained, a label for that brain state is comprised in a target label and is indicated in matrix Y to be affirmative or active at least during the time corresponding to the specific portion of the original data. An affirmative label represents a training state.

The tradeoff constant, alpha, is a weight indicating the desired relative accuracy of the modeling of data in matrix X 110 in comparison to the modeling of matrix Y 150. For example, when forming sparse matrices U 130, V 120 and W 140 alpha indicates the desired relative accuracy of modeling of matrix X 110 in relation to the accuracy of modeling matrix Y 150.

$C_u$, $C_v$ and $C_w$ are regularization constants that are weights on the L1-penalty for the matrices U 120, V 130 and W 140, respectively, and are used as constants in a penalized loss function, for example, the loss function described below by EQ. 1. The loss function is a negative log-likelihood of an overall model that includes both the GLM model for matrix X 100 given matrix U 130, and the GLM model for matrix Y 150 given matrix U 130. Regularization comprises the weighted sum of L1-penalties over each of the matrices U 130, V 120 and W 140. Each L1-penalty is the sum of the absolute values of the elements of the corresponding matrix, and the weights are the regularization constants. For each matrix, the weight can be different and is given by the constants $C_u$, $C_v$ and $C_w$ for matrices U 130, V 120 and W 140, respectively. The regulation constants $C_u$, $C_v$ and $C_w$ control the level of sparsity, e.g., the number of nonzero elements in the solution to the above optimization problem, of matrices U 130, V 120 and W 140, respectively. Regulation constants are further described by the paper previously cited: Tibshirani, R, *Regression Shrinkage and Selection via the Lasso*.

The loss difference threshold epsilon is the desired maximum difference in regularized total loss between successive iterations of iterative optimization of the regularized total loss, for example, as calculated in method 400 presented below.

Step 302 comprises forming the predictive model by learning or forming matrices U 130, V 120 and W 140 such that the matrices U 130, V 120 and W 140 provide a substantially minimized regularized total loss. The forming of matrices U 130, V 120 and W 140 comprises component analysis (e.g., principle or independent component analysis) for extracting hidden components from the training data. Note that a minimized regularized loss may, for example, correspond to a maximized negative log likelihood. Thus, providing a substantially minimized regularized loss may be done by substantially maximizing a negative log likelihood. The total loss, for example, may be expressed by the loss function:

$$L(U,V,W) = L_x(X,UV) + \text{alpha} * L_y(Y,UW) + C_u|U|_1 + C_v|V|_1 + C_w|W|_1. \quad \text{EQ. 1}$$

L(U,V,W) is the total loss metric corresponding to matrices U 110, V 120 and W 140 (e.g., negative log likelihood). $L_x(X, UV)$ is the regularized loss for matrix X 110 given matrices U 130 and V 120. $L_y(Y,UW)$ is the regularized loss for matrix Y 150 given matrices U 130 and W 140. For EQ. 1, the tradeoff constant, alpha is the ratio of the desired accuracy of modeling matrix Y 150 to the modeling of matrix X 110. For example, if alpha=0.5, the accuracy of modeling matrix Y 150 is only half as important as the accuracy of modeling matrix X 100. By way of example only, forming matrices U 130, V 120 and W 140 such that the matrices U 130, V 120 and W 140 provide a substantially minimized regularized total loss may comprise repeated or iterative application of sparse regression methods (e.g., L1 regularization methods, for example L1 regularization methods comprising error calculations comprising summing absolute values of components within a matrix, such as matrix X 100 and/or matrix Y 150).

Forming the predictive model comprises extracting or determining components of the training data that are not readily observable in the training data. Regression analysis is used to extract the one or more hidden components from the training data. The regression analysis comprises determining relationships between the hidden components and training data, and determining relationships between the hidden components and the training states. The number of the hidden components is less than the number of variables in the training data and greater than the number of the training states.

In step 303, the matrices U 130, V 120 and W 140 are returned to the model completing the learning phase.

Figure 4:
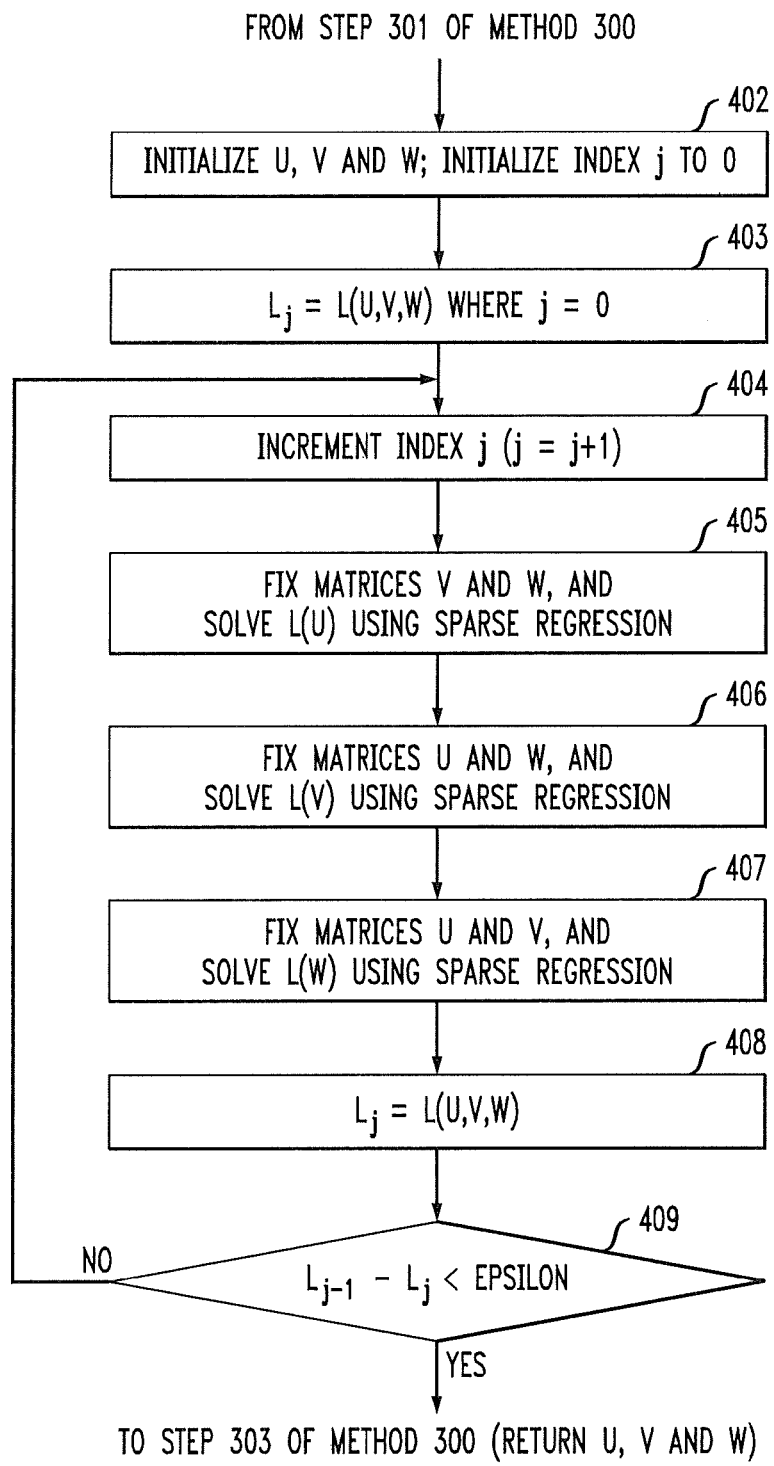
FIG. 4 illustrates an iterative optimization method for learning a sparse supervised component model according to an exemplary embodiment of the invention.

FIG. 4 illustrates an iterative optimization method for learning a sparse supervised component model 400 according to an embodiment of the invention. Step 302 of method 300 (learning or forming matrices U 130, V 120 and W 140) may comprise, for example, the iterative optimization method 400.

Step 402 comprises initializing (calculating) matrices U 130, V 120, and W 140. Matrices U 130, V 120 and W 140 may be initialized to, or calculated to have, random values. Alternately, matrices U 130, V 120 and W 140 may be initialized to values according to prior knowledge, which may be incomplete or inaccurate prior knowledge. Initializing is considered to be an initial calculation. Initializing to random values or to a number is considered to be initially calculating to set to random values or to a number. As an example, prior knowledge for fMRI based predictions may be prior knowledge of voxel activation patterns (e.g., patterns that are to be further formed or refined). Step 402 further comprises initializing an iteration or loop index j to 0 (j=0). The iteration index, j, indicates the current regularized total loss calculation in the sequence of iterations (loops) of current regularized total loss calculations. The initialization and the corresponding initial regularized total loss calculation corresponds to j=0.

Step 403 comprises calculating the regularized total loss for the initialized matrices U 130, V 120 and W 140 for the initial iteration (j=0), $L_0=L(U,V,W)$ according to the previously presented equation EQ. 1.

Step 404 comprises advancing the index j by 1, that is j=j+1.

Step 405 comprises, given the current matrices V 120 and W 140 (i.e., fix or leave unchanged current matrices V 120 and W 140 at current values), learn or solve for (recalculate) matrix U 130 using L1 regularized regression (i.e., sparse regression) or other sparse regression method. Learning or solving for matrix U 130 may comprise, for example, minimizing regularized loss for matrix U 130.

Step 406 comprises, given the current matrices U 130 and W 140 (fix or leave unchanged current matrices U 130 and W 140 at current values), learn or solve for (recalculate) matrix V 120 using L1 regularized regression (i.e., sparse regression) or other sparse regression method. Learning or solving for matrix V 120 may comprise, for example, minimizing regularized loss for matrix V 120.

Step 407 comprises, given the current matrices U 130 and V 120 (fix or leave unchanged current matrices U 130 and V 120 at current values), learn or solve for (recalculate) matrix W 140 using L1 regularized regression (i.e., sparse regression) or other sparse regression method. Learning or solving for matrix W 140 may comprise, for example, minimizing regularized loss for matrix W 140.

Step 408 comprises calculating an updated or latest regularized total loss for the latest learned matrices U 130, V 120 and W 140 ($L_j=L(U,V,W)$) according to equation EQ. 1.

Step 409 comprises calculating a difference in the regularized total losses between the prior regularized total loss ($L_{j-1}$) and the latest regularized total loss ($L_j$). If the calculated difference is less than the predetermined threshold epsilon, method 400 terminates and returns learned matrices U 130, V 120 and W 140 (step 303 of method 300). If the latest calculated difference is greater than the threshold epsilon, steps 404 through 409 repeat or iterate as indicated in FIG. 4.

Method 400 keeps repeating or iterating steps 404 through 409 until the latest calculated difference is less than the threshold epsilon.

Regression analysis is used to learn the mapping between the variables of the original or training data and the components (i.e., hidden components of matrices V 120, U 130 and W 140) and the mapping between the target labels or training states and the components. Matrix V 120 comprises the mapping between the components and the variables of the original or training data, and matrix W 140 comprises the mapping between the components and the training states.

Figure 5:
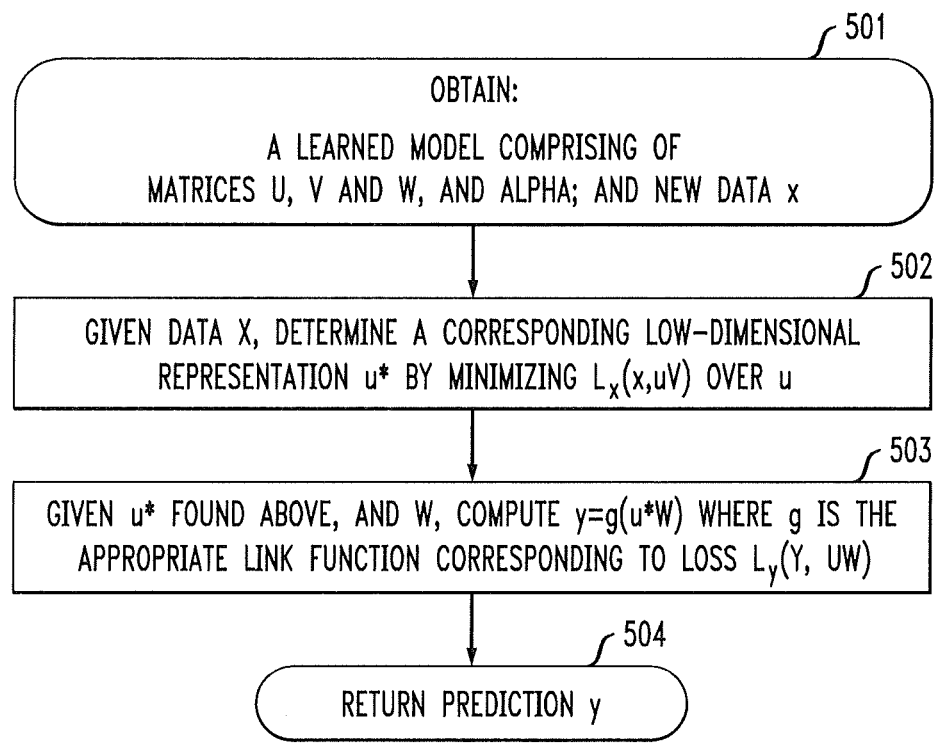
FIG. 5 illustrates a method of prediction based upon a learned sparse supervised component model according to an exemplary embodiment of the invention.

FIG. 5 illustrates a method of prediction 500 based upon the learned SSC model according to an embodiment of the invention. Method 500 may be considered an implementation of step 220 of method 200. Matrices U 130, V 120 and W 140 have already been learned, for example, according to methods 300 and 400.

Step 501 comprises obtaining a learned model and new data (x), and providing the new data to the model. The learned model may be, for example, the SSC model having parameters learned in step 210 of method 200. The learned model may comprise learned matrices U 130, V 120 and W 140 and the tradeoff constant, alpha. By way of example only, the new data may comprise data from a test subject, for example, brain fMRI data from the test subject, the fMRI data representing a particular point in time. The new data may comprise a vector of length D (i.e., data of size 1×D). The test subject may be a subject about which a prediction y may be made. The prediction may be made according to the new data (x).

Step 502 comprises determining a corresponding low-dimensional representation u* of data x by minimizing a regularized loss function, $L_x(x, uV)$, for data x while keeping data x constant and at the obtained values and keeping matrix V 120 constant with the values obtained in step 501. u* is a vector of components having length L (i.e., a vector having dimensions 1×L). The L entries in u* are components similar to the components of matrix U 130. The regularized loss function may be minimized by regression analysis.

Step 503 comprises computing y=g(u*W), where g is the appropriate link function corresponding to the regularized loss $L_y(Y, UW)$ for matrix Y 150 given matrices U 130 and W 140 (see step 302 of method 300). u* has been determined in step 502. W 140 was learned in step 210 of method 200. y is a vector of target labels having length K (i.e., a vector having dimensions 1×K). The K target labels are similar to the target labels of matrix Y 150, for example, each of the target labels of y is a predictor of a state of the subject, for example, a predictor of a brain state of the subject.

Step 504 comprises returning (i.e., providing) the prediction y.

Consider the following non-limiting example. A test subject suspected of having a brain disease (e.g., mental, emotional or organic brain disease) undergoes fMRI brain imaging. Test data x is produced from the imaging. A model (e.g., a GLM or another sparse regression model including tradeoff constant alpha, link function g, and matrices U 130, V 120 and W 140) has previously been established to be predictive of brain diseases schizophrenia, depression, dementia and narcolepsy. The model was formed according to methods of the invention, for example, step 210 of method 200. The model comprises four target labels (K=4) with one target label corresponding to each of the above brain disease. The first target variable is predictive of schizophrenia. The second target variable is predictive of depression. The third target variable is predictive of dementia, and the fourth target variable is predictive of narcolepsy. In a first case, if the calculated vector y=(0, 1, 0, 1), the model predicts that the subject has depression and narcolepsy. In a second case, if the calculated vector y=(0, 0, 1, 0), the model predicts that the subject has dementia. Furthermore predictions by the model may or may not indicate exclusion. In the second case, where vector y=(0, 0, 1, 0), the prediction may only indicate that the subject is suffering from dementia and not indicate whether or not the subject is suffering from schizophrenia, depression or narcolepsy. Alternately, in the second case, where vector y=(0, 0, 1, 0), the prediction may indicate not only that the subject is suffering from dementia, but that the subject does not have schizophrenia, depression or narcolepsy. Methods of the invention and predictive models according to embodiments of the invention may be considered to be diagnostic of disease, brain and other states or conditions and may be considered to be biomarkers.

Figure 6:
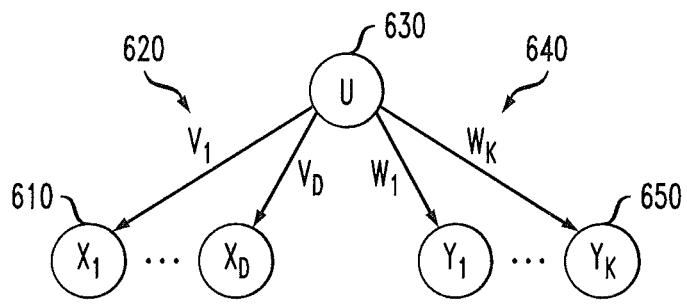
FIG. 6 is a diagram of an exemplary generalized linear model according to an embodiment of the invention.

FIG. 6 presents a diagram of an exemplary GLM 600 according to an embodiment of the invention. The GLM 600 comprises matrix U 630 which is similar and performs the same function as matrix U 130. The GLM 600 further comprises: matrix X comprising D columns (variables) 610 comprising columns (variables) $X_1$ through $X_D$; matrix Y comprising K columns (labels) 650 comprising columns (labels) $Y_1$ through $Y_D$; matrix V comprising D columns (variables) 620 comprising columns (variables) $V_1$ through $V_D$; and matrix W comprising K columns (labels) 640 comprising columns (labels) $W_1$ through $W_K$. Thus, $X_d$ is the column vector for the d-th column of matrix X 110, $V_d$ is the column vector for the d-th column of matrix V 120, $W_k$ is the column vector for the k-th column of matrix W 140, and $Y_k$ is the column vector for the k-th column of matrix Y 150.

As indicated in the diagram of the GLM 600, $X_d$ may be formed from U according to $V_d$, for d from 1 to D. Also as indicated in the diagram of the GLM 600, $Y_k$ may be formed from U according to $W_k$, for k from 1 to K. The exemplary GLM 600 may be expressed by the following equations.

$$E(X_d) = f_d^{-1}(UV_d) \qquad \text{EQ. 2}$$

$$E(Y_k) = f_k^{-1}(UW_k) \qquad \text{EQ. 3}$$

$E(X_d)$ is the expected value of $X_d$ for d=1 to D. $UV_d$ is a predictor (e.g., a linear predictor). $f_d^{-1}$ is the inverse of function $f_d$. $f_k^{-1}$ is the inverse of function $f_k$. Functions $f_d$ and $f_k$ are link functions of GLMs and are defined, for example, by a corresponding exponential family. For one example, either or both of $f_d$ and $f_d$ may be an identity function $f(\mu)=\mu$ associated with a Gaussian distribution and linear regression. For another example, either or both of $f_d$ and $f_d$ may be a logit $f(\mu)=\log \mu/(1-\mu)$ function associated with a Bernoulli, binominal or multinomial distribution and logistic regression.

The GLM regression may be applied separately to each column of matrix X 110 and to each column of matrix Y 150. In one embodiment of the invention, the same GLM regression (e.g., corresponding to a common link function) is applied to each column of matrix X 110. However, in a different embodiment of the invention, different GLM regressions (e.g., corresponding to different link functions) may be applied to different columns of matrix X 110. Similarly, same or different GLM regressions may be applied to different columns of matrix Y 150. For example, different regressions, link functions or inverse link functions may be applied to different columns of a matrix (e.g., matrix X 110 or matrix Y 150) if different column of the matrix correspond to variables may of different types. For example, a set of columns in matrix X 110 may contain only real-valued (i.e., analog) data from fMRI image, and an additional set of columns in matrix X 110 may contain binary variables (e.g., whether a subject was tired or not at the time of fMRI imaging). Furthermore, the output/label predicted variables in matrix Y 150 may also be both binary type (e.g., seeing the presence or absence of an image or a sentence on a screen) and real-valued type (e.g., indicating a level of anxiety on an analog scale).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring again to FIGS. 1 through 6, the diagrams in the figures illustrate the architecture, functionality, and operation of possible implementations of systems, methods and computer program products according to various embodiments of the present invention. In this regard, each block in a flowchart or a block diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts, or combinations of special purpose hardware and computer instructions.

Accordingly, techniques of the invention, for example, as depicted in FIGS. 1-6, can also include, as described herein, providing a system, wherein the system includes distinct modules (e.g., modules comprising software, hardware or software and hardware). By way of example only, the modules may include: a training data obtaining module configured to obtain training data comprising a plurality of variables; a training states obtaining module configured to obtain one or more training states associated with the training data; a predictive model forming module configured to form a predictive model according to the training data and the one or more training states, the predictive model predictive of the one or more training states; a subject data obtaining module configured to obtain predictive data from the subject; and a predicting module configured to predict one or more states of the subject, the one or more states of the subject comprise the one or more training states. These and other modules may be configured, for example, to perform the steps of described and illustrated in the context of FIGS. 1-6.

Figure 7:
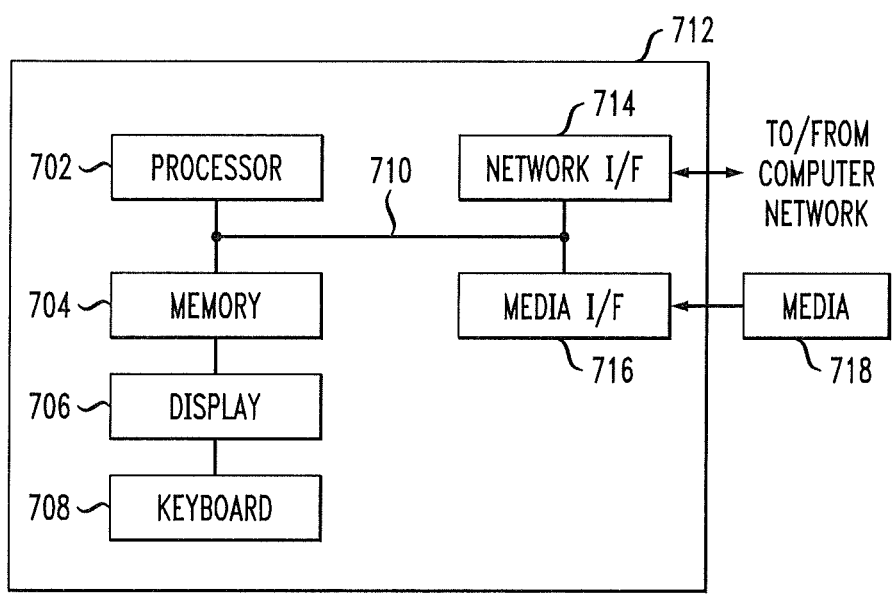
FIG. 7 illustrates a computer system in accordance with which one or more components/steps of the techniques of the invention may be implemented according to an embodiment of the invention.

One or more embodiments can make use of software running on a general purpose computer or workstation. With reference to FIG. 7, such an implementation 700 employs, for example, a processor 702, a memory 704, and an input/output interface formed, for example, by a display 706 and a keyboard 708. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, keyboard or mouse), and one or more mechanisms for providing results associated with the processing unit (for example, display or printer). The processor 702, memory 704, and input/output interface such as display 706 and keyboard 708 can be interconnected, for example, via bus 710 as part of a data processing unit 712. Suitable interconnections, for example, via bus 710, can also be provided to a network interface 714, such as a network card, which can be provided to interface with a computer network, and to a media interface 716, such as a diskette or CD-ROM drive, which can be provided to interface with media 718.

A data processing system suitable for storing and/or executing program code can include at least one processor 702 coupled directly or indirectly to memory elements 704 through a system bus 710. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboard 708, display 706, pointing device, and the like) can be coupled to the system either directly (such as via bus 710) or through intervening I/O controllers (omitted for clarity).

Network adapters such as network interface 714 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 712 as shown in FIG. 7) running a server program. It will be understood that such a physical server may or may not include a display and keyboard.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for predicting one or more states of a subject, the method comprising:
    obtaining training data comprising a plurality of variables;
    obtaining one or more training states associated with the training data; and
    forming a predictive model according to the training data and the one or more training states, the predictive model being predictive of the one or more training states, wherein the forming of the predictive model comprises extracting one or more hidden components from the training data, wherein the extracting of the one or more hidden components comprises regression analysis comprising determining one or more relationships between the one or more hidden components and the plurality of variables, and determining one or more relationships between the one or more hidden components and the one or more training states, and wherein a number of the one or more hidden components is less than a number of the plurality of variables and greater than a number of the one or more training states;
    wherein the one or more training states comprise one or more predicted brain states of the subject comprising at least one of: a mental state, a cognitive state, a disease state, a response to a stimulus, a response to a physical task, a response to a mental task, a response to an emotion, and a response to a sensatory input;
    wherein the extracting of the one or more hidden components comprises reducing a regularized total loss comprising a regularized loss of a first matrix comprising the training data and a regularized loss of a second matrix comprising the one or more training states;
    wherein one or more of the obtaining of the training data, the obtaining of the one or more training states, and the forming of the predictive model are implemented as instruction code executed on a processor device.

2. The method of claim 1, wherein the predicting of the one or more states of the subject comprises regression analysis comprising determining one or more relationships between a representation of the predictive data and the predictive data according to the predictive model.

3. The method of claim 1, wherein the reducing of the regularized total loss comprises at least one of: (i) a maximizing log-likelihood calculation for a loss function; and (ii) a minimizing negative log-likelihood calculation for a loss function.

4. The method of claim 1, wherein the regression analysis comprises at least one of: (i) linear regression; (ii) sparse regression; (iii) a least squares method; (iv) a least absolute shrinkage and selection operator (Lasso) method; (v) L1-regularization; (vi) an Elastic Net method; (vii) a group least absolute shrinkage and selection operator (group Lasso) method; and (viii) a generalized linear model.

5. The method of claim 1, wherein the regression analysis comprises assigning non-zero weights to predictive variables of the plurality of variables that are predictive of the training states.

6. The method of claim 1, wherein the regression analysis is used to learn a mapping between the plurality of variables and the one or more hidden components and a mapping between the one or more training states and the one or more hidden components.

7. A system for predicting one or more states of a subject, the system comprising:
- a training data obtaining module configured to obtain training data comprising a plurality of variables;
- a training states obtaining module configured to obtain one or more training states associated with the training data; and
- a predictive model forming module configured to form a predictive model according to the training data and the one or more training states, the predictive model being predictive of the one or more training states, wherein the forming of the predictive model comprises extracting one or more hidden components from the training data, wherein the extracting of the one or more hidden components comprises regression analysis comprising determining one or more relationships between the one or more hidden components and the plurality of variables, and determining one or more relationships between the one or more hidden components and the one or more training states, and wherein a number of the one or more hidden components is less than a number of the plurality of variables and greater than a number of the one or more training states;
- wherein the one or more training states comprise one or more predicted brain states of the subject comprising at least one of: a mental state, a cognitive state, a disease state, a response to a stimulus, a response to a physical task, a response to a mental task, a response to an emotion, and a response to a sensatory input;
- wherein the extracting of the one or more hidden components comprises reducing a regularized total loss comprising a regularized loss of a first matrix comprising the training data and a regularized loss of a second matrix comprising the one or more training states;
- wherein one or more of the obtaining of the training data, the obtaining of the one or more training states, and the forming of the predictive model are implemented as instruction code executed on a processor device.

8. An apparatus for predicting one or more states of a subject, the apparatus comprising:
- a memory; and
- a processor coupled to the memory and configured to:
- obtain training data comprising a plurality of variables;
- obtain one or more training states associated with the training data; and
- form a predictive model according to the training data and the one or more training states, the predictive model being predictive of the one or more training states, wherein the forming of the predictive model comprises extracting one or more hidden components from the training data, wherein the extracting of the one or more hidden components comprises regression analysis comprising determining one or more relationships between the one or more hidden components and the plurality of variables, and determining one or more relationships between the one or more hidden components and the one or more training states, and wherein a number of the one or more hidden components is less than a number of the plurality of variables and greater than a number of the one or more training states;
- wherein the one or more training states comprise one or more predicted brain states of the subject comprising at least one of: a mental state, a cognitive state, a disease state, a response to a stimulus, a response to a physical task, a response to a mental task, a response to an emotion, and a response to a sensatory input;
- wherein the extracting of the one or more hidden components comprises reducing a regularized total loss comprising a regularized loss of a first matrix comprising the training data and a regularized loss of a second matrix comprising the one or more training states.

9. An article of manufacture for predicting one or more states of a subject, the article of manufacture comprising a non-transitory computer readable storage medium tangibly embodying a computer readable program code which, when executed, causes the computer to:
- obtain training data comprising a plurality of variables;
- obtain one or more training states associated with the training data; and
- form a predictive model according to the training data and the one or more training states, the predictive model being predictive of the one or more training states, wherein the forming of the predictive model comprises extracting one or more hidden components from the training data, wherein the extracting of the one or more hidden components comprises regression analysis comprising determining one or more relationships between the one or more hidden components and the plurality of variables, and determining one or more relationships between the one or more hidden components and the one or more training states, and wherein a number of the one or more hidden components is less than a number of the plurality of variables and greater than a number of the one or more training states;
- wherein the one or more training states comprise one or more predicted brain states of the subject comprising at least one of: a mental state, a cognitive state, a disease state, a response to a stimulus, a response to a physical task, a response to a mental task, a response to an emotion, and a response to a sensatory input;
- wherein the extracting of the one or more hidden components comprises reducing a regularized total loss comprising a regularized loss of a first matrix comprising the training data and a regularized loss of a second matrix comprising the one or more training states.

* * * * *